(12) United States Patent
Chappa et al.

(10) Patent No.: US 10,238,844 B2
(45) Date of Patent: *Mar. 26, 2019

(54) METHOD AND APPARATUS FOR COATING BALLOON CATHETERS

(71) Applicant: Surmodics, Inc., Eden Prairie, MN (US)

(72) Inventors: Ralph A. Chappa, Ham Lake, MN (US); Mark F. Carlson, St. Louis Park, MN (US)

(73) Assignee: Surmodics, Inc., Eden Praire, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/434,556

(22) Filed: Feb. 16, 2017

(65) Prior Publication Data

US 2017/0157372 A1 Jun. 8, 2017

Related U.S. Application Data

(63) Continuation of application No. 14/641,109, filed on Mar. 6, 2015, now Pat. No. 9,579,491, which is a
(Continued)

(51) Int. Cl.
*B05B 13/02* (2006.01)
*B05B 13/04* (2006.01)
(Continued)

(52) U.S. Cl.
CPC .... *A61M 25/1029* (2013.01); *A61M 25/1018* (2013.01); *B05B 13/0214* (2013.01); *B05B 13/0228* (2013.01); *B05C 13/00* (2013.01); *B05D 1/002* (2013.01); *B05D 1/02* (2013.01); *B05D 3/12* (2013.01); *A61M 25/1027* (2013.01);
(Continued)

(58) Field of Classification Search
USPC ....... 118/300, 313, 315, 319, 320, 321, 500, 118/501, 306, 317; 427/2.1, 256, 258, 427/261, 402, 421.1, 424, 427.1; 623/1.1, 623/192, 198, 108, 194
See application file for complete search history.

(56) References Cited

U.S. PATENT DOCUMENTS 3,745,840 A 7/1973 Guralnick
4,613,329 A 9/1986 Bodicky
(Continued)

FOREIGN PATENT DOCUMENTS

EP 1 834 636 9/2007
WO 2007/084418 7/2007

*Primary Examiner* — Yewebdar T Tadesse
(74) *Attorney, Agent, or Firm* — Kagan Binder, PLLC

(57) ABSTRACT

A coating apparatus for coating the balloon portion of a balloon catheter is described. The coating apparatus includes a rotatable member in which the catheter portion of the balloon catheter is mounted and fixed, and which causes rotation of the balloon catheter. The apparatus also includes a support member in which the distal tip of the catheter is inserted and free to rotate; and a spray nozzle directing sprayed material on the balloon surface. The inventive configuration of the coating apparatus allows the balloon catheter to be rotated along its axis with insubstantial or no wobble, which significantly improves the quality of the coating applied to the surface of the balloon.

10 Claims, 4 Drawing Sheets

Related U.S. Application Data continuation of application No. 12/583,112, filed on Aug. 14, 2009, now Pat. No. 9,295,820.

(60) Provisional application No. 61/188,929, filed on Aug. 14, 2008.

(51) Int. Cl.
*A61M 25/10* (2013.01)
*B05D 1/00* (2006.01)
*B05D 1/02* (2006.01)
*B05C 13/00* (2006.01)
*B05D 3/12* (2006.01)

(52) U.S. Cl.
CPC ............ *A61M 2025/105* (2013.01); *A61M 2025/1031* (2013.01)

(56) References Cited

U.S. PATENT DOCUMENTS

| | | | |
|---|---|---|---|
| 5,102,402 A | 4/1992 | Dror et al. | |
| 5,272,012 A | 12/1993 | Opolski | |
| 5,304,121 A | 4/1994 | Sahatjian | |
| 5,340,433 A * | 8/1994 | Crump | B22F 3/115 118/202 |
| 5,429,606 A | 7/1995 | Robinson et al. | |
| 5,520,664 A | 5/1996 | Bricault, Jr. et al. | |
| 5,674,192 A | 10/1997 | Sahatjian et al. | |
| 5,882,336 A | 3/1999 | Janacek | |
| 5,954,706 A | 9/1999 | Sahatjian | |
| 6,129,705 A | 10/2000 | Grantz | |
| 6,143,037 A | 11/2000 | Goldstein et al. | |
| 6,364,893 B1 | 4/2002 | Sahatjian et al. | |
| 6,394,995 B1 | 5/2002 | Solar et al. | |
| 6,395,326 B1 | 5/2002 | Castro et al. | |
| 6,562,136 B1 | 5/2003 | Chappa et al. | |
| 6,623,504 B2 | 9/2003 | Vrba et al. | |
| 6,638,246 B1 | 10/2003 | Naimark et al. | |
| 7,060,051 B2 | 6/2006 | Palasis | |
| 7,077,910 B2 | 7/2006 | Chappa et al. | |
| 7,125,577 B2 | 10/2006 | Chappa | |
| 7,192,484 B2 | 3/2007 | Chappa et al. | |
| 7,416,609 B1 | 8/2008 | Madriaga et al. | |
| 7,638,344 B2 | 12/2009 | Slager et al. | |
| 7,758,605 B2 | 7/2010 | McMorrow et al. | |
| 8,051,797 B1 | 11/2011 | Teichman et al. | |
| 9,292,820 B2 | 3/2016 | Williams | |
| 9,579,491 B2 * | 2/2017 | Chappa | B05B 13/0214 |
| 2003/0064965 A1 | 4/2003 | Richter | |
| 2003/0129130 A1 | 7/2003 | Guire et al. | |
| 2003/0207019 A1 | 11/2003 | Shekalim et al. | |
| 2004/0247775 A1 | 12/2004 | Boulais et al. | |
| 2005/0158449 A1 | 7/2005 | Chappa | |
| 2005/0220843 A1 | 10/2005 | DeWitt et al. | |
| 2005/0244459 A1 | 11/2005 | DeWitt et al. | |
| 2006/0110209 A1 | 5/2006 | Shekalim et al. | |
| 2006/0280858 A1 | 12/2006 | Kokish | |
| 2007/0053953 A1 | 3/2007 | Verlee et al. | |
| 2007/0128343 A1 | 6/2007 | Chappa | |
| 2008/0311805 A1 * | 12/2008 | Spears | B63B 22/08 441/30 |
| 2009/0028956 A1 | 1/2009 | Slager et al. | |
| 2009/0246252 A1 | 10/2009 | Arps et al. | |

\* cited by examiner

METHOD AND APPARATUS FOR COATING BALLOON CATHETERS

CROSS-REFERENCE TO RELATED APPLICATION

This application is a continuation of application Ser. No. 14/641,109, filed Mar. 6, 2015, which is a continuation of application Ser. No. 12/583,112, filed Aug. 14, 2009, now U.S. Pat. No. 9,295,820, which claims priority under 35 U.S.C. § 119(e) from U.S. Provisional Patent Application having Ser. No. 61/188,929, filed on Aug. 14, 2008, and titled METHOD AND APPARATUS FOR COATING BALLOON CATHETERS, wherein the entirety of said patent applications are incorporated herein by reference.

FIELD OF THE INVENTION

The invention relates to a spray coating apparatus and methods for disposing a coating material on a medical device surface.

BACKGROUND OF THE INVENTION

Functional improvements to implantable or insertable medical devices can be achieved by coating the surface of the device. For example, a coating formed on the surface of the device can provide improved lubricity, improved biocompatibility, or drug delivery properties to the surface. In turn, this can improve movement of the device in the body, extend the functional life of the device, or treat a medical condition near the site of implantation. However, various challenges exist for the design and use of coating apparatus designed to provide coatings to medical devices.

Traditional coating methods, such as dip coating, are often undesirable as they may result in flawed coatings that could compromise the function of the device or present problems during use. These methods can also result in coating inaccuracies, which can be manifested in variable amounts of the coated material being deposited on the surface of the device. When a drug is included in the coating material, it is often necessary to deliver precise amounts of the agent to the surface of the device to ensure that a subject receiving the coated device receives a proper dose of the agent. It has been difficult to achieve a great degree of accuracy using traditional coating methods and machines.

As another challenge, implantable or insertable medical devices are typically small and often have unusual, complex configurations. As a general matter, the handing of these devices in an appropriate manner during a coating procedure is often challenging.

Spray coating techniques have been used to apply coating material to various devices, including medical devices. See, for example, U.S. Pat. Nos. 6,562,136, 7,077,910, 7,125,577, and 7,192,484. In some cases, a coating process involves repetitively applying a coating material to a fixtured device in order to achieve a target quantity and quality of coated material. Devices are often manipulated between the applications of the coating material and dried to a certain extent before these manipulations are performed. It is often difficult to fixture and manipulate the devices so they receive a desired coating of material. It is also often difficult to prevent the coating apparatus and method from introducing defects into the formed coating.

One type of insertable medical device is a balloon catheter. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Balloon catheters generally include four portions, the balloon, catheter shaft, guidewire, and manifold. A balloon catheter generally includes an elongated catheter shaft with an inflatable balloon attached to a distal section of the catheter shaft. At a proximal end of the catheter shaft, there is typically a manifold. At the manifold end, placement of the catheter can be facilitated using a guidewire. Guidewires are small and maneuverable when inserted into an artery. Once the guidewire is moved to the target location, the catheter with balloon portion is then fed over the guidewire until the balloon reaches the target location in the vessel. The balloon is typically inserted into the arterial lumen of a patient and advanced through the lumen in an unexpanded state. The balloon is then inflated when the catheter reaches target site resulting in application of mechanical force sufficient to cause vessel dilation. The balloon is typically inflated using a fluid, which is injected through an inflation port. The manifold can control the fluid introduction within shaft for expansion of the balloon. The mechanics of fluid transfer and introduction within balloons vary according to the specific design of the catheter, and are well know in the art.

Applicants have found that the complex design of a balloon catheter has made the balloon portion of the catheter difficult to coat. Accordingly, Applicants have provided new equipment and methods useful for overcoming the problems associated with the spray coating of medical devices, such as balloon catheters.

SUMMARY

The invention generally relates to an apparatus and methods for coating an implantable or insertable medical device. In embodiments of the invention, the methods and apparatus are directed towards coating an insertable medical device having an expandable elastic portion, such as a balloon catheter.

In one aspect, the invention provides a coating apparatus for rotatably coating an insertable or implantable medical device, such as a balloon catheter. The coating apparatus includes a rotatable member in which a catheter portion of a balloon catheter can be fixed and rotated. The rotatable member has an elongate shape with a distal end, a proximal end, and a central axis. The central axis of the rotatable member is accessible, and the catheter portion can be fixed in the rotatable member along the central axis so the catheter axis is aligned with the central axis. The coating apparatus also includes a support member having an aperture that is aligned with the central axis of the rotatable member. The support member is capable of holding the distal tip of the balloon catheter, but allows for rotation of the balloon catheter when the catheter portion is fixed and rotated by the rotatable member. The distal end of the rotatable member is separated from the support member by a gap. The gap has a length sufficient to accommodate the length of the balloon portion of the balloon catheter. The coating apparatus also includes a spray nozzle capable of delivering a spray of coating material in the gap between the distal end of the rotatable member and the support member. When a balloon catheter is mounted in position, the spray nozzle can deliver a spray of coating material to the balloon surface.

The invention also provides a method for spray coating a material on the surface of a portion of a balloon catheter. The method includes a step of providing a balloon catheter comprising a catheter portion having a catheter axis, a balloon portion, and a distal tip. The balloon catheter is then mounted in a coating apparatus having a rotatable member, a support member, and a spray nozzle. In the step of mounting, a part of the catheter portion is fixed by the rotatable member, so that the catheter axis is aligned with the central axis of the rotatable member. The step of mounting also includes inserting the distal tip of the balloon catheter in the support member so that it is held, but free to rotate in place. With the catheter portion fixed, and distal tip supported, the balloon catheter is straightened and rotatable along the central axis. In another step, the balloon catheter is rotated about its central axis. In another step, a coating of material is applied to the surface of the balloon from a spray nozzle.

Generally, the distance between the distal end of the rotatable member and the support member is the same or greater than the distance of the balloon portion as measured along the catheter axis.

In some aspects, the support member comprises a grommet in which the distal tip of the catheter is held and rotatable in. In some aspects, the support member is rotatable.

In some aspects the apparatus further includes a drive mechanism that can drive rotation of the rotatable member. Preferably, the drive mechanism is mechanically coupled to the rotatable member. For example, the drive mechanism can be coupled to the proximal end of the rotatable member.

In some aspects, the coating nozzle is movable in a direction along the central axis of the apparatus, which is in line with the central axis of the rotatable member. Accordingly, in one preferred aspect of the coating process, the spray nozzle is moved along the length of the balloon portion of the balloon catheter. In some cases the steps of disposing the coating material and moving the spray nozzle are performed simultaneously.

In some aspects the apparatus further includes a balloon inflation device (e.g., Indeflator™). The balloon inflation device can be used for insertion or removal of gas from the balloon portion of the balloon catheter. Accordingly, in some aspects, the method includes a step of inflating the balloon portion of the balloon catheter. In some aspects, the method includes applying a coating of material to the surface of the balloon when the balloon is inflated. The tip of the spray nozzle can be positioned at an appropriate distance from the balloon surface to provide a desired application of coating material on the surface.

The balloon catheter can be rotated by the rotatable member in a continuous or an intermittent manner. In some aspects, the balloon catheter is continuously rotated while a spray of coating material is deposited on the balloon surface. For intermittent rotation, the rotatable member can be coupled to a drive mechanism having an indexing function.

The invention provides advantages for the coating of medical devices, in particular balloon catheters. For example, the apparatus improves a balloon catheter coating process because the spraying of the entire circumference of the balloon surface can be carried out with rotational movement, and during the rotation there is little or no deviation in the distance between the balloon surface and the tip of the spray nozzle. As such, the coating apparatus and method can provide precise positioning and uniform rotation of the balloon catheter with respect to the spray head. This is achieve because the rotatable member and support member are arranged and are able to secure the balloon catheter in such a way that the axis of the balloon catheter remains straight during the rotational movement, thereby preventing unsteady or wobbly rotation of the balloon. This ultimately provides a more uniform coating because there is minimal variance of the distance between the tip of the coating nozzle and the surface of the balloon being coated while the balloon catheter is being rotated.

In addition, the apparatus is advantageous in that it can allow for rapid loading and removal of pre-inflated balloon catheters without coiling or kinking the of the catheter portions.

In addition, the apparatus is advantageous in that it can protect the catheter from extraneous coating flux.

DETAILED DESCRIPTION OF THE INVENTION

Figure 1:
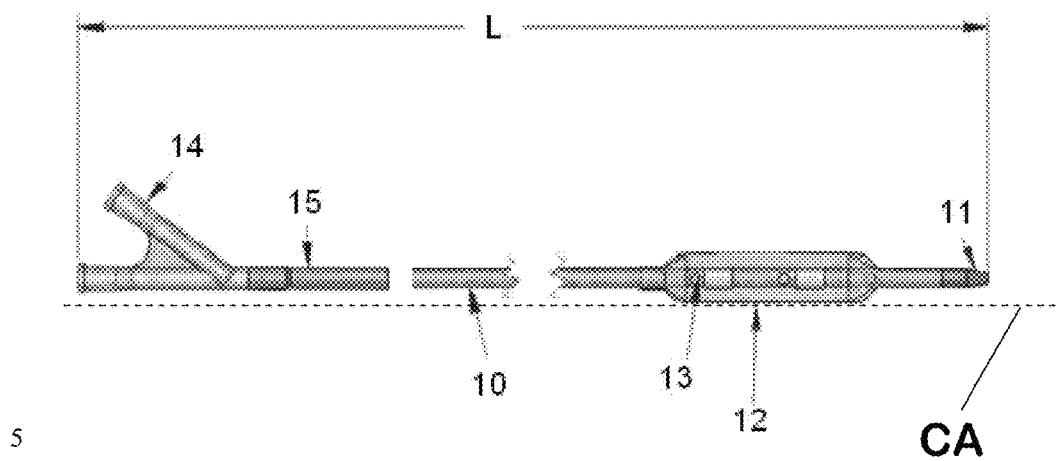
FIG. 1 is an illustration of a standard balloon catheter.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

One aspect of the present invention relates to an apparatus for coating a balloon catheter. The apparatus includes a rotatable member, a support member, and a spray nozzle. The rotatable member and support member are arranged along the same axis of rotation (herein referred to as the "central axis") and are separated by a gap. The gap between the rotatable member and support member is large enough to accommodate a balloon portion (lengthwise) of a balloon catheter. The rotatable member can also secure or fix the catheter portion of the balloon catheter in place so that it can be rotated about its axis (i.e., the catheter axis), which is also coincident with the central axis of the device. The rotatable member can include a cavity that runs along the central axis in which the catheter portion of the balloon catheter can be placed and then secured. The rotatable member can have a cylindrical or tubular shape. The rotatable member can also be mechanically associated with a drive mechanism that can be actuated to promote rotational movement of the rotatable member.

The support member can hold the distal end (tip) of the balloon catheter in place so that the balloon catheter is essentially straight from its proximal end to its distal end. This can ensure that rotation of the balloon catheter can be performed with essentially little or no wobble, which, in turn, improves the spray coating process.

The spray nozzle is configured to produce a spray of a coating material that is directed towards the gap between the rotatable member and support member. When the catheter portion of the balloon catheter is fixed by the rotatable member and the distal tip is held by the support member, and when the spray nozzle is actuated, the balloon surface can be coated with coating material. The coating process can be carried out while the balloon catheter is rotated, which can cause the coating material to be deposited about the periphery of the balloon. Also, the spray nozzle can be movable in a direction along the central axis of the device. The spray nozzle can be moved in proximal to distal, and/or distal to proximal directions along the central axis when the spray nozzle is actuated to provide a coating to the surface of the balloon.

In some modes of practice, a coating process can involve applying the coating material multiple times (i.e., multiple applications of a coating material) on the surface of the balloon while the balloon catheter is being rotated. For example, with movement of the spray nozzle, the coating material can be applied from the spray nozzle from the distal end of the balloon portion to its proximal end (or from the distal to proximal end) on one portion of the balloon surface. The device can be rotated and then the coating material can be applied again along another portion of the balloon surface. These applications of coating material can be repeated to provide a coating on the balloon surface with a desired amount of coating material.

In some modes of practice, the same or overlapping portions of the device are coated multiple times in order to produce a balloon surface having a desired quality or quantity of coating material. For example, after a portion of the balloon surface is coated with a first application of a coating material, the balloon catheter is then rotated to place the surface in position for a subsequent application of a coating material. Rotation of the balloon catheter can be continuous or intermittent.

The coating apparatus and/or method of the invention can be used to prepare coatings described in commonly assigned U.S. patent application Ser. No. 12/383,751, filed on Mar. 27, 2009 (Arps et al.).

In order to describe the invention in greater detail, reference to the following illustrations are made. The illustrations are not intended to limit the scope of the invention in any way but are to demonstrate some of the various embodiments of the coating apparatus and its features.

First, in order to explain the details of the coating apparatus and method, reference is made to a standard balloon catheter, as shown in FIG. 1. A standard balloon catheter includes a catheter body 10 (tubing/shaft) that extends most or all of the length (L) of the device, a tip 11 at the distal end of the device, a balloon portion 12 which can be inflated, an inflation aperture 13 for the balloon, and an inflation port 14 at the proximal (user) end. Although the catheter body runs most of the length of the device, for purposes of discussion, the "catheter portion" of the device refers to that between the point where the inflation port meets the catheter body and the proximal end of the balloon.

Figure 3:
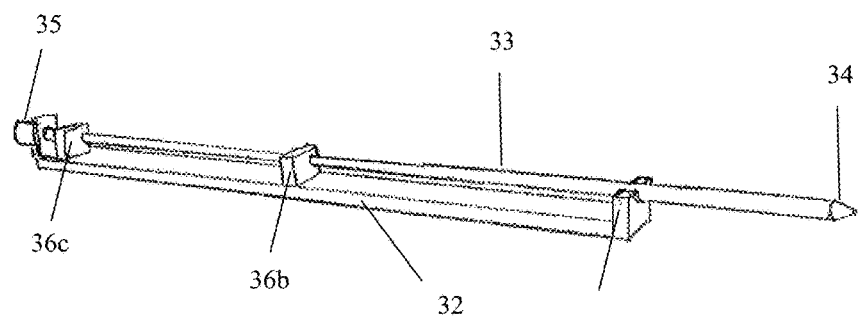
FIG. 3 is an illustration of an embodiment of the rotatable member.

The catheter body is typically flexible so that it can navigate through the arterial system when introduced into a subject. A more rigid portion 15 of the catheter is proximal to the inflation port 14. The catheter body (from proximal to distal end) can be straightened so the catheter follows a linear path. The catheter body can be held in a straightened configuration using the coating apparatus, as described herein. When the catheter body is straightened along a linear path, the catheter can have an axis "catheter axis" CA about which the catheter can be rotated when mounted in the coating apparatus of the invention. The length (L) of balloon catheters can vary; standard lengths being in the range of about 50 cm to about 150 cm.

In one embodiment, the coating apparatus includes a rotatable member, a support member, and a spray nozzle. FIG. 2 shows the apparatus 20 with a mounted catheter 21. The coating apparatus 20 according to the invention can include a housing 22 on which the coating process can be performed. Mounted to a portion of the housing is the rotatable member 23 (a distal portion of the rotatable member 23 is shown), which can be used to fix at least a part of the catheter portion of the balloon catheter near the balloon portion and rotate the balloon catheter about the central axis. The rotatable member 23 is shown having a cylindrical shape and is tapered at its distal end 24.

The rotatable member 23 is attached to rotatable member mounting units **26*a* and 26*b* that support the rotatable member in a horizontal position. The rotatable member mounting units are attached at their bases to the housing 22**.

As shown in FIG. 2, the rotatable member 23 has a central axis that runs parallel to the catheter portion 21 of the balloon catheter when the catheter is fixed in place. The rotatable member 23 includes a central portion which encompasses the central axis of the rotatable member and that can accommodate the catheter portion 21 of the balloon catheter. When the catheter portion 21 is fixed in placed within the central portion of the rotatable member 23, as shown in FIG. 2, the axis of the catheter is aligned with the central axis of the rotatable member 23. Since the catheter axis is aligned with the central axis, upon rotation there is no, or negligible, wobble of the balloon catheter.

The apparatus 20 also includes a distal tip support member 27, (also referred to as "support member" herein) which is shown in as a part of a support member mounting unit 28. The support member 27 can support the distal end (tip) of the balloon catheter 25 and allow it to rotate freely when the balloon catheter is rotated. The support member mounting unit 28 is shown attached at it base to the housing 22. Optionally, the distal tip support member 27 can rotate freely in the support member mounting unit 28.

The apparatus 20 also includes a spray mechanism, the spray nozzle 29 of which is shown. The spray nozzle 29 is able to produce a spray SP of coating material that is directed at the surface of the balloon portion 30 of the balloon catheter when mounted in the apparatus.

The rotatable member is able to fix the catheter portion of the balloon catheter in place and rotate it for the spray coating process. Since, generally, the catheter portion of the balloon catheter is long, the rotatable member can also be long to accommodate the catheter portion. For example, the rotatable member can have a length similar to that of the overall length of the balloon catheter.

An illustration of an entire rotatable member 33 is shown in FIG. 3.

The rotatable member can be of any suitable size and shape to fix the catheter portion in place and cause rotational movement of the balloon catheter. In many aspects, the rotatable member has an elongated shape. The elongated shape can include a cylindrical shape (viewed in cross section), such as shown in FIGS. 2 and 3, providing the outer surface of the rotatable member 33 with a curved surface. However, other shapes that provide the rotatable member with one or more flat outer surfaces are contemplated. Viewed as a cross-section of the rotatable member, the other shapes may be polygonal (hexagonal, octagonal, etc.). In some aspects, the rotatable member may also have one or more different shapes along its length. For example, as shown in FIG. 3, the rotatable member 33 has a cylindrical shape towards the distal end of the apparatus, and a shape that is partially cylindrical (such as half a cylinder) towards the proximal end of the apparatus.

A rotatable member 33 with a fully cylindrical-shaped distal end can protect the catheter portion of the balloon catheter (proximal to the balloon portion) from any extraneous coating flux during the spray coating process. Further, and as a general matter, a fully cylindrically shaped distal end can facilitate the fixation of at least the part of the catheter portion near the balloon so the catheter body is aligned with the central axis of the rotatable member.

The distal end 34 of rotatable member can also be tapered. As shown in FIG. 3, the distal end has a conical shape.

In many aspects, the rotatable member has a cross-sectional diameter in the range of about 2 cm to about 10 cm. In an exemplary design, the cross-sectional diameter is about 4 cm. In many aspects, the rotatable member has a length from the proximal end to the distal end in the range of about 50 cm to about 200 cm; in an exemplary design, the length is about 100 cm.

As shown in FIG. 3, the rotatable member 33 is attached to rotatable member mounting units 36a, 36b, and 36c that hold the rotatable member in a horizontal position and that are attached to the housing 32.

Figure 4:
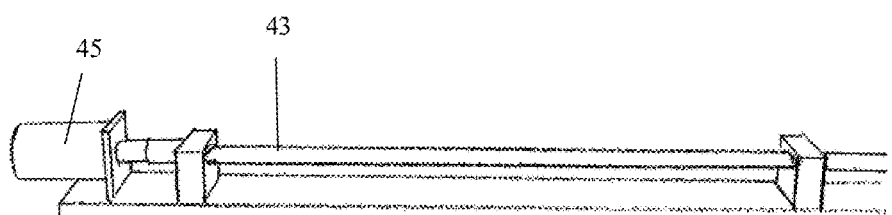
FIG. 4 is another illustration of an embodiment of the rotatable member.

The proximal portion of the coating apparatus is shown in greater detail in FIG. 4. FIG. 4 illustrates a drive mechanism 45 that is directly connected to the rotatable member 43. The drive mechanism can include any suitable motor (such as a standard DC motor) to drive movement of the rotatable member.

Alternatively, the drive mechanism can be indirectly mechanically associated with the rotatable member. For example, one or more components (e.g., a drive shaft, belt, etc.) can be located between the drive mechanism and the rotatable member to translate movement and cause rotation of the rotatable member.

The drive mechanism can optionally have an indexing function that allows for intermittent rotation of the rotatable member. Intermittent rotation can be useful during the spray coating processes wherein partial rotation of the device is performed after a spray coating of material is applied to the device. An indexing function of the roller drive mechanism will be described in greater detail below.

The rotatable member can also include a central portion that accommodates the catheter portion of the balloon catheter. The rotatable member can have a design so its central portion is accessible and the catheter portion can be placed in alignment with the central axis of, and fixed within, the rotatable member.

Figure 5A:
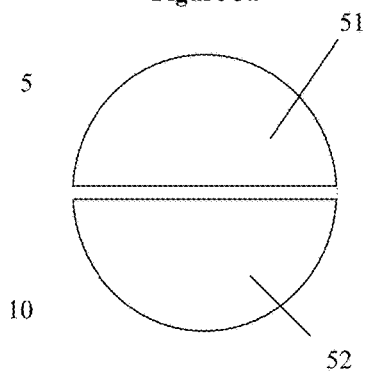
FIGS. 5a, 5b, and 5c are illustrations of cross sections of the rotatable member as viewed from its distal end.

In some aspects, at least the distal portion of the rotatable member is configured so the central portion can be accessed. In one aspect, at least the distal portion of the rotatable member is split along its length (from proximal to distal ends). For example, the rotatable member can have a split cylindrical configuration, as shown in FIG. 5a (as viewed from proximal or distal ends). One half 51 of the split cylinder can be separated from the other half 52 to expose the central portion. For example, in one arrangement, the two half cylinders can be hinged along one side to allow for opening and closing of the rotatable member.

Figure 5B:
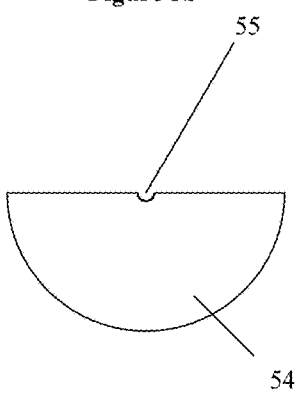
Figure 5C:
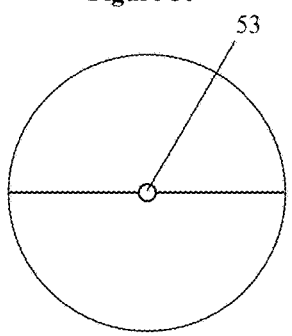

In some aspects, at least the distal portion of the rotatable member includes a cavity that can accommodate the catheter portion of the balloon catheter. The cavity can be of a suitable shape and configuration to accommodate the catheter portion of the balloon catheter in the rotatable member. Generally, along at least a part of the length of the rotatable member, the cavity is elongate and has a curved inner surface, sufficient to accommodate the catheter portion. For example, referring to FIG. 5c, as viewed from the proximal or distal end of the rotatable member, the cavity 53 can have a circular shape (when the split cylindrical halves are placed together); FIG. 5b shows one half 54 of a split cylinder with a semicircular cavity 55. In some cases, the cavity forms an opening at the distal end of the rotatable member having a diameter in the range of about 0.1 cm to about 1.0 cm in diameter, with 0.3 cm being a typical diameter. In many cases the cavity can have a shape that fits the shape of the outside of the catheter portion of the balloon catheter.

The rotatable member can be formed of any suitable durable material, for example, stainless steel, polyoxymethylene (POM) (e.g., Delrin), acrylonitrile butadiene styrene (ABS), polyvinyl chloride (PVC), polycarbonates, polysulfones, or glass.

Referring back to FIG. 1, the coating apparatus 20 according to the invention includes a support member 27. The support member 27 can support the distal end 25 of the balloon catheter (i.e., the tip of the balloon end of the device) so the catheter can be maintained in a linear configuration and the balloon catheter can be rotated about its axis when rotation of the device is commenced. Essentially, the distal tip of the device is held in the support member, but is allowed to rotate freely. The support member can include a low friction material that contacts the surface of the distal end 25 of the balloon catheter, the low friction material facilitating the overall rotation of the balloon catheter.

The center of the support member 27 is aligned with the central axis of the rotatable member 23.

Figure 6:
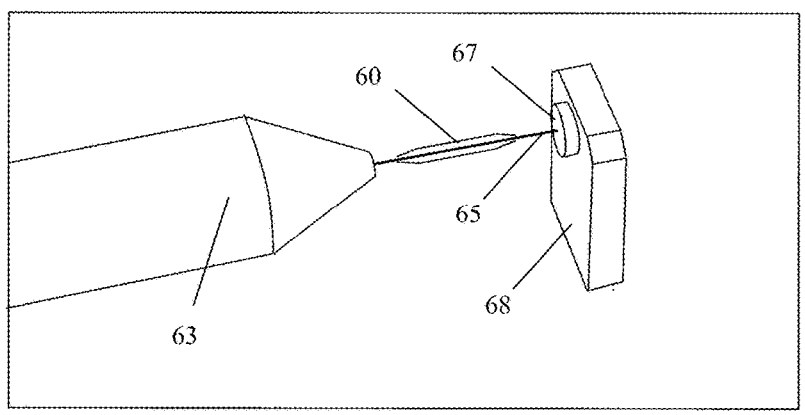
FIG. 6 is an illustration of the distal portion of the rotatable member, the support member, and a mounted balloon catheter.

As shown in greater detail in FIG. 6, in some designs of the coating apparatus, the support member 67 is mounted in or on a support member mounting unit 68 that holds the support member 67 in a horizontal position. FIG. 6 also shows that a proximal part of the catheter portion fixed in the rotatable member 63. The balloon portion 60 therefore becomes positioned between the distal end of the rotatable member 63 and the support member 67.

As shown in FIG. 6, the support member 67 has a circular shape and is held within a recess in the support member unit 68. As shown in FIG. 6, the tip of the balloon catheter is held in the center of the support member 67. The support member 67 can be in the form of a grommet or eyelet. The center of the support member 67 can have an orifice or aperture into which the distal end (tip) 65 of the balloon catheter is placed. For example, the grommet can have a center that is configured to receive the distal end 65 of the catheter and hold it in place during rotation of the catheter. The orifice or aperture preferably has a diameter in the range of about 0.1 cm to about 2.0 cm, with an exemplary diameter being about 0.3 cm.

Optionally, the support member can be rotatable along with the balloon catheter. In this case, the support member could be a second rotatable member of the device, with the part of the apparatus that fixes the catheter portion being a first rotatable member. If the support member is rotatable it can also be configured to secure the distal end of the balloon catheter. For example, the support member can have a clamping feature so that when the distal end of the balloon catheter is inserted in the center of the support member, it cannot easily be pulled out of place. The clamping feature may be provided by forming the support member out of an elastomeric material into which the distal end of the balloon catheter can be inserted and held. For example, the support member can include a rubber ring with a hole in the center, the hole being smaller than the diameter of the distal end of the balloon catheter. When the distal end of the balloon catheter is inserted into the hole in the ring, pressure is applied to the outer surface of the distal end of the balloon catheter, which holds the distal end in place. This secures the distal end (tip) of the catheter and prevents it from moving in a proximal to distal or distal to proximal directions when the balloon catheter is mounted in the apparatus. Rotation of the support member 67 can be facilitated by including bearings, or the like, around the member to minimize any resistance to rotational movement. Optionally, the rotation of the support member 67 can be facilitated by mechanically coupling the support member to a drive mechanism. If the support member is coupled to a drive mechanism, it can be the same drive mechanism that drives rotation of the rotatable member.

Optionally, the coating apparatus can include more than one pair of the rotatable member and the support member. Having multiple pairs of the rotatable and support members can be useful to increase process throughput if it desired to provide coatings to a plurality of balloon catheters. Multiple rotatable members can be aligned on the apparatus so their central axes are parallel to each other. Multiple support members can be arranged so they are aligned with the central axes of each respective rotatable member. Balloon catheters can be loaded into each pair of rotatable and support members. Other configurations of multiple rotatable and support members are contemplated, such as those wherein pairs of multiple rotatable and support members are movable on the surface of the coating apparatus, such as in a track system, to bring a pair of members into a coating zone for the application of a coating.

If the apparatus includes more than one pair of rotatable and support members, one or both member of the pair can be mechanically associated with a common drive member. For example, a common drive member can be mechanically connected to multiple rotatable members, and can cause rotation of all of the rotatable members when actuated.

A single coating nozzle can be used for the coating of multiple balloon catheters. Function and movement of the spray coating nozzle in aspects of the invention having rotatable and support members are described in greater detail herein.

Figure 2:
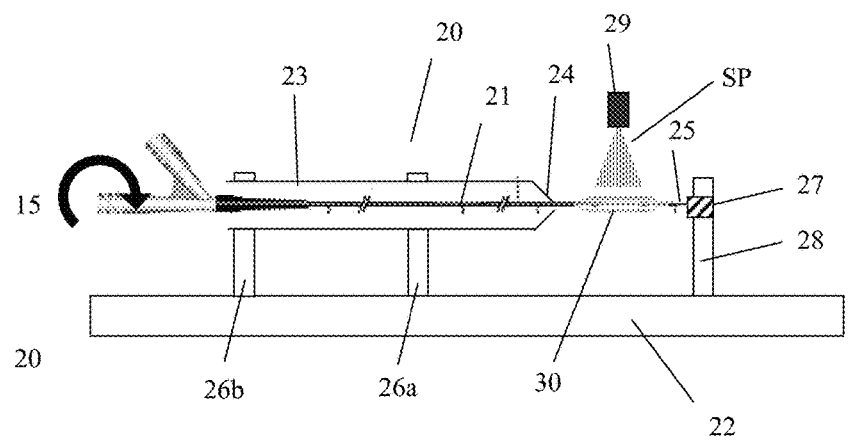
FIG. 2 is an illustration of a cross section of one embodiment of the coating apparatus with a mounted balloon catheter.

The coating apparatus also includes a spray nozzle configured to produce a spray of coating material which can be deposited on the balloon surface of the balloon catheter when mounted in the apparatus for a spray coating process. As shown in FIG. 2, the spray nozzle 29 is arranged on the coating apparatus to delivery a spray of coating material SP between the distal end of the rotatable member 24, and the proximal face of the support member 27. When the balloon catheter is mounted in the apparatus, the nozzle can deliver a spray of coating material to the balloon surface. The area in which the spray of material is applied can be referred to as the "coating zone." The coating zone is an area where the spray coating process takes place and in which spray nozzle is movable.

Figure 7:
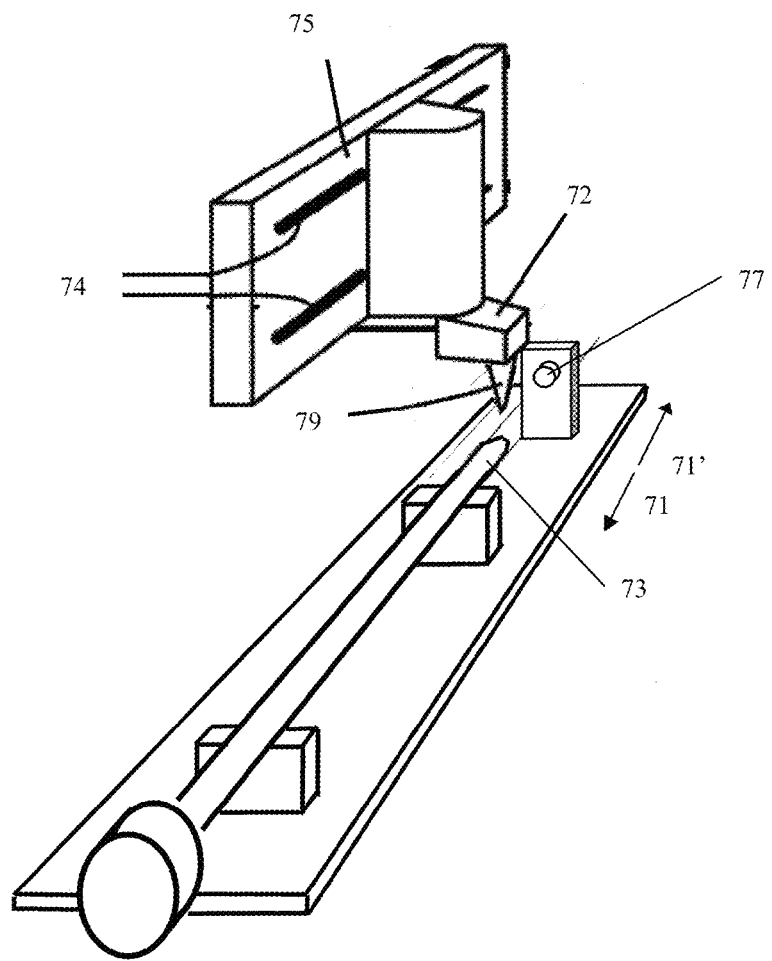
FIG. 7 is an illustration of an embodiment of the coating apparatus showing the rotatable member, the support member, and a spray nozzle attached to a movable track.

Referring to FIG. 7, the spray nozzle 79 can be mounted on an arm 72 so that the spray nozzle 79 is appropriately positioned relative to the rotatable member 73 and the support member 77. The arm 72 can be adjustable to provide a desired distance between the balloon surface (when the balloon catheter is mounted on the coating apparatus) and the tip of the spray nozzle 79, from which the spray of coating material emanates. (Without the balloon catheter mounted in the apparatus, the positioning of the spray nozzle can also be described as the distance between the tip of the spray nozzle and the imaginary line that represents the central axis of the first and support member.)

In many aspects, the tip of the spray nozzle is positioned close to the central axis of the coating apparatus. For example, the distance between the tip of the spray nozzle and the central axis is in the range of about, 5 mm to about 25 mm, more specifically in the range of about 5 mm to about 10 mm, or in one exemplary embodiment about 8 mm.

In many aspects of the invention, the spray nozzle is movable. For example, as shown in FIG. 7, the spray nozzle 79 is movable in directions parallel to the central axis as shown by arrows 71 and 71'. In one arrangement, the spray nozzle 79 is mounted on an arm 72, and a portion of the arm 72 is within a track 74 in a mounting unit 75 which allows the arm 72 to moves in a direction along the central axis. The track 74 can include a motorized unit that controls the movement of the arm 72, and thus movement of the spray nozzle 79 in relation to the balloon catheter that is mounted in position. A track motor (not shown) can drive the movement of the arm 72, via a belt, chain, pulley, cord, or gear arrangement.

As such, the spray nozzle can be movable to provide a coating of spray material along the length of the surface of the balloon providing a "stripe" of coating material deposited along a portion of the surface of the balloon from one end to the other end of the balloon. The stripe of deposited coating material has a width that is typically a fraction of the circumference of the balloon. During the spray coating process, the balloon catheter can be rotated as desired, and the step of depositing coating material can be repeated.

In some aspects of the invention, the spray nozzle is configured to produce a spray of coating material having a narrow spray pattern. As used herein, "spray pattern" refers to the shape of the body of coating material sprayed from the spray nozzle. "Spray" or "sprayed material" refers to the droplets of coating material that are produced from the spray nozzle.

Various types of spray nozzles can be used in association with the coating apparatus of the invention. In one preferred aspect, the spray nozzle includes a sonicating member, and conduits for solution (coating material) delivery and air delivery. One exemplary spray nozzle with a sonicating member is the MicroFlux XL nozzle sold by SonoTek (Milton, N.Y.). In a sonicating spray coating method, a coating solution is delivered via a solution delivery line (not shown) to the tip of the spray nozzle. The spray nozzle includes an air delivery/sonicating member. At the tip of the nozzle, the solution (coating material) is sonicated by the sonicating member, which produces droplets of solution. The droplets are drawn into and carried by the gas stream originating at the tip of the spray nozzle.

The spray pattern produced by this type of sonicating nozzle is considerably narrower than many other spray patterns generated from traditional types of spray nozzles. For example, when positioned at a distance of about 0.8 cm from the coating (e.g., balloon) surface, this type of spray nozzle provides a coating of material on the surface of the balloon that has a width of approximately 1-2 mm.

Delivery of the coating material in the form of a spray can be affected by various operational aspects of the sonicating nozzle. These include the rate of delivery of the solution, the size of the orifice of the solution delivery member, the distance of the solution delivery member from the tip of the sonicator/air delivery member, the tip size and configuration of the sonicator, the amount of energy provided to the sonicator, the size of the orifice at the outlet of the gas channel, the rate of delivery of gas from the gas delivery port (air pressure), and the type of gas delivered from the spray nozzle.

Other types of spray nozzles can be used in the coating apparatus. For example, another type of spray nozzle that can be used in the coating apparatus is a jet nozzle. Suitable jet nozzles, for example, jet nozzles found in ink jet printers, can be obtained from The Lee Company (Westbrook, Conn.). Various types of ink jet nozzles are contemplated, for example, thermal inkjet nozzles which utilize thermal energy to emit solution from the nozzle via a pressure wave caused by the thermal expansion of the solution; electrostatic inkjet nozzles wherein a solution is emitted from the nozzle by electrostatic force; piezoelectric inkjet nozzles in which solution is ejected by means of an oscillator such as a piezoelectric element; and combinations of these types of inkjet nozzles.

In some exemplary modes of practice, the operating conditions for application of a spray coating on the surface of the balloon are: about 0.03 mL/min of sprayed coating material delivered from the nozzle at a pressure of about 2.5 psi, with a balloon rotation speed of about 300 RPM.

If the apparatus includes more than one set of rotatable and support members aligned in parallel, the spray nozzle can be movable in directions both parallel (according to arrows 71 and 71') and perpendicular to the central axes of the rotatable and support members. The spray nozzle can be moved perpendicularly to place the nozzle tip in line with the central axis of the desired rotatable and support members.

The loading or mounting of the balloon catheter in the coating apparatus can be carried out manually. For example, the balloon catheter can be loaded into the apparatus using the following procedure: First, the rotatable member is placed in a position so the central portion is accessible. For example, if the rotatable member has a split-cylinder configuration (such as a split-cylinder configuration that is opened using a hinge system) the cylinder can be opened to expose its central portion, which can be a cavity that is coincident with the central axis of the rotatable member. The catheter portion of the balloon catheter can then be laid in line with the central axis of the rotatable member and fixed in place. In some modes of practice, the catheter portion is placed in a cavity (such as one shown in FIGS. 5*b* and 5*c*), which is preferably of a size and configuration to accommodate the catheter portion. Next, the tip of the balloon catheter is placed in the support member so that the distal end of the catheter is secured, yet free to rotate. For example, the tip is placed in the center of a grommet or eyelet made of elastomeric material. The tip is secured in the grommet or eyelet by pressure exerted around the periphery of the tip (i.e., the tip tightly fits within the grommet). At that point, and before closing the split cylinder of the rotatable member, the balloon catheter is straightened to ensure the catheter portion is taut, and the axis of the balloon catheter is in alignment with the central axis of the rotatable member. After the balloon catheter has been properly positioned, the rotatable member can be closed which fixes the balloon catheter in place for rotation.

It is contemplated that the steps in the mounting process can be modified, or the order of the steps changed, while still ultimately securing the balloon catheter for rotation in the apparatus, so the axis of the balloon catheter coincides with the central axis of the device.

Inflation of the balloon portion of the balloon catheter can be performed prior to the spray coating process. In some modes of practice, inflation of the balloon portion is performed after the balloon catheter is mounted in the device, but before the spray coating process begins. However, the balloon portion can be inflated at any time, such as before the balloon catheter is mounted, or even during the coating process.

Referring back to FIG. 1, the proximal end of the catheter typically includes an indeflation port 14. For inflation of the balloon portion 12, the indeflation port 14 can be connected to a standard balloon inflation device (e.g., Indeflator™). The balloon portion 12 can then be inflated, which causes expansion of the balloon portion 12 to its predetermined shape. Preferably, the balloon portion 12 is inflated using a gas, such as air. A fully inflated balloon pressure generally ranges from about 6 atm to about 12 atm, with a standard inflated balloon pressure being about 8 atm. The balloon can be inflated to a predetermined pressure prior to the coating process.

A particular pressure can be chosen so the balloon inflates to a predetermined size for the coating process. During the coating process, the inflated size may be (a) less than the size of the balloon when inflated at the target site in the body, (b) the same size as the balloon when inflated at the target site in the body, or (c) greater than the size as the balloon when inflated at the target site in the body. In some modes of practice, during the coating process, the size of the balloon is the same, or less than the size of the balloon when inflated at the target site in the body.

In some embodiments of the invention, the coating process is carried out when the balloon is inflated to a pressure that is less than the fully inflated pressure. For example, the balloon has a fully inflated pressure of about 8 atm, and the coating process is carried out when the balloon is inflated to a pressure of less than about 8 atm.

In one mode of practice, the balloon is inflated to a size that is less than the size of the balloon when inflated at the target site in the body, and then the surface of the balloon is coated. This mode of practice can be desirable for forming coatings which are designed to fracture upon inflation to the target size in vivo, wherein portions of the fractured coating are released from the balloon surface and provide a therapeutic effect to the patient at the target site. That is, the balloon is provided with a coating when the balloon surface has a first surface area (and then the coating has this surface area as well), and then, when placed at a target location in the body, the coating is expanded to size that provides a second surface area, which is greater than the first surface area. As such, this causes the coating to fracture, which in turn promotes delamination of the coating from the surface of the balloon.

In some modes of practice, the spray nozzle can be moved along the central axis while providing a spray of coating material that is directed at the balloon surface. This results in a portion of the balloon surface being coated and provides a "stripe" of coating material deposited along a portion of the length of the balloon. The stripe of deposited coating material has a width that is typically a fraction of the circumference of the balloon surface. The balloon can be rotated as desired and the step of depositing coating material on the balloon surface can be repeated. The step of depositing can be carried out a number of times to provide a coating having properties as desired.

In many cases a step of depositing coating material will result in the application of coating material over a previously applied area of coating material. Deposition of the coating material and rotation of the balloon catheter can be carried out so the coating material dries between applications, or partially dries between applications of the coating material. "Dry" or "dried" refers to the condition of the coated portion of the balloon surface, wherein the coated portion is not tacky and wherein most of any solvent in the coated portion has evaporated from the balloon surface.

The apparatus and methods of the invention allow for the improved spray coating of a balloon portion of a balloon catheter. Improvements in the coating process can be reflected by, for example, in the uniformity of the applied coating, the consistency in the amount of applied coating, the protection of other parts of the balloon catheter to obstruct deposition of the coating material, and the increased throughput of the coating process.

The apparatus and method of the invention can be used to form a coating on the surface of a balloon portion of a balloon catheter wherein the coating has one or more desired properties. The invention contemplates methods for forming coatings on the balloon surface with any type or types of materials that can be delivered from the spray nozzle. The coating process is not limited to any particular coating material. In many aspects, the coating process involves deposition of a coating composition that includes one or more polymeric material(s) on the surface of the balloon. Exemplary polymeric materials for coating the surface of a balloon are described in commonly assigned U.S. patent application Ser. No. 12/383,751, filed on Mar. 27, 2009 (Arps et al.). Typically, the balloon is formed of an elastomeric material, and a coating can be formed on an elastomeric surface to change its surface properties. For example, a coating formed on the surface of the device can provide a lubricious surface, which in turn can facilitate movement of the balloon surface when the balloon catheter is inserted in the body. As another example, the coating can provide a biocompatible surface (i.e., a biocompatible surface being one that does not have an adverse biological effect on the tissue which it is in contact with). In yet other embodiments, the coating method provides a coating on the balloon surface that releases, or facilitates the release of, a bioactive agent.

The method can be used to form a coating that includes one or more coated layers. In a single "coated layer" the materials deposited on the surface form a film/stratum wherein substantially or entirely the same materials are present. A single coated layer can also have a certain thickness. In some mode of practice, while the method may involve a plurality of depositions of coating material on the surface of the balloon, if the same coating material is used in the process and the process results in a generally uniform material on the surface, the coating can be considered to have one coated layer.

In some aspects, the coating includes a bioactive agent-releasing layer. A bioactive agent-releasing layer can be adjacent to one or more other coated layers which can optionally be present in the coating. (For purposes of discussion, and also to describe various aspects of the invention, the coated layers may be described by a "first coated layer", a "second coated layer", and, so forth. For example, when describing a coating with two layers, whether a "first layer" is distal or proximal to the surface of the device will be understood in the context of the specific description of that coating.)

In some aspects, the coating apparatus is used to form a coating on the surface of a balloon with microparticles embedded in the coating. A microparticle-containing coating can be formed to include biodegradable polymers, biostable polymers, or combinations of both. The coating can also include a biodegradable polymeric layer which covers the microparticles.

The apparatus can form a coating wherein the microparticles are the particulate components that include bioactive agent, and which are releasable from the elastic surface of the device. The microparticles can be any three-dimensional particle of size and shape sufficient to be associated with the surface of the elastic substrate using the coating materials, and then dissociated upon its expansion of the substrate.

Microparticles may have a spherical, or substantially spherical shape, such as those that are formed from synthetic polymeric materials. In many aspects, the elastic portion of the device is associated with spherical or substantially spherical microparticles. However, microparticles associated with a balloon surface can have noticeably non-spherical shapes or irregular shapes (for example, when examined by microscopy). For example, microparticles can have curved surfaces, flat surfaces, or combinations thereof. If desired, the expandable elastic portion can be associated with a plurality of microparticles of a combination of different sizes and/or shapes.

In many aspects, microparticles associated with the expandable elastic portion using the apparatus and/or method of the invention have an average diameter ("dn", number average) that is less than about 50 µm. Also, in many aspects, the microparticles can have an average diameter of about 100 nm or larger. For example, the microparticles associated with the expandable elastic portion can have an average diameter in the range of about 100 nm to about 50 µm, about 150 nm to about 25 µm, about 200 nm to about 20 µm, or about 0.3 µm to about 10 µm.

Depending on the manner by which the microparticles are associated with the elastic portion, it can be desirable to use microparticles within a particular size range. For example, when the microparticles are immobilized in a coating on the surface of the elastic portion, it is generally desirable to utilize microparticles having an average diameter that is smaller than the thickness of the coating.

In the least, the microparticles that are associated with the expandable elastic substrate using the apparatus and/or method of the invention include a bioactive agent. Therefore, in some embodiments, the microparticles can be formed completely or substantially of a selected bioactive agent for treatment or prevention of a condition. In other embodiments, the microparticles can be formed from a combination of bioactive agents (e.g., two or more different bioactive agents). In other embodiments, the microparticles can be formed from a bioactive agent and another component that is not intended to provide a therapeutic effect to the subject, such as a polymer that can modulate the release of the bioactive agent from the microparticles. In other embodiments the microparticles include two or more components, such as two or more polymers that modulate the release of the bioactive agent from the microparticle.

Components of the microparticle can be in mixture with one another in a portion of, or all of, the microparticle. Alternatively, the components can be entirely or substantially separated from one another in the microparticle. For example, the microparticle can be formed comprising a substantially homogenous mixture of a bioactive agent and a release-modulating polymer. As another example, the microparticle can be formed comprising a bioactive agent core and a release-modulating polymer shell around the core.

The coating apparatus and/or method of the invention can be used to prepare microparticle-containing coatings as described in commonly assigned U.S. patent application Ser. No. 12/383,751, filed on Mar. 27, 2009 (Arps et al.).

The term "bioactive agent," refers to an inorganic or organic molecule, which can be synthetic or natural, that causes a biological effect when administered in vivo to an animal, including but not limited to birds and mammals, including humans. A partial list of bioactive agents is provided below. One may choose any one of the bioactive agents to be included in a microparticle set alone, or in combination with any other bioactive agent. A comprehensive listing of bioactive agents, in addition to information of the water solubility of the bioactive agents, can be found in The Merck Index, Thirteenth Edition, Merck & Co. (2001).

The microparticles, which are released from the elastic substrates, can be used to deliver bioactive agents falling within one or more of the following classes, which include, but are not limited to, ACE inhibitors, actin inhibitors, analgesics, anesthetics, anti-hypertensives, anti polymerases, antisecretory agents, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, anti-viral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, prostaglandins, remodeling inhibitors, statins, steroids, thrombolytic agents, tranquilizers, vasodilators, and vasospasm inhibitors.

In some aspects the microparticles comprise an antiproliferative agent. The antiproliferative agent can be an antiangiogenesis agent.

In some aspects the microparticles comprise an anti-inflammatory agent.

In some aspects the microparticles comprise a cell response modifier.

In some aspects the microparticles comprise an antithrombotic agent.

In some aspects the microparticles comprise an immunosuppressive agent.

What is claimed is:

1. An apparatus for coating a balloon catheter, the apparatus comprising:
   (a) a rotatable member comprising an elongated shape having an elongated split cylindrical configuration with a distal end and a proximal end, a central axis about which the rotatable member can be rotated and which is configured to accommodate and fix a catheter portion of a balloon catheter having a catheter axis so the central axis is aligned with the catheter axis;
   (b) a support member, which is aligned with the central axis of the rotatable member, which is configured to hold and allow rotation of a distal tip of the balloon catheter when the catheter portion of the balloon catheter is fixed and rotated in the rotatable member, and wherein the distal end of the rotatable member is separated from the support member by a gap; and
   (c) a nozzle capable of delivering coating material in the gap between the distal end of the rotatable member and the support member.

2. The apparatus of claim 1 wherein the elongated split cylindrical configuration is split along its length from proximal to distal ends.

3. The apparatus of claim 2 wherein the rotatable member comprises two half cylinders hinged along one side of the rotatable member.

4. The apparatus of claim 1 wherein the support member comprises a circular grommet.

5. The apparatus of claim 1 wherein the rotatable member has a length in the range of 50 cm to 200 cm.

6. The apparatus of claim 1 wherein the nozzle comprises a spray nozzle.

7. The apparatus of claim 1 further comprising an indeflator.

8. The apparatus of claim 1 further comprising a drive mechanism which causes rotation of the rotatable member, support member, or both.

9. The apparatus of claim 8 wherein the drive mechanism is attached to the proximal end of the rotatable member.

10. The apparatus of claim 1 wherein the support member comprises a low friction material.

* * * * *